United States Patent
Schoenberg

(10) Patent No.: US 7,172,120 B2
(45) Date of Patent: Feb. 6, 2007

(54) METHOD OF AND SYSTEM FOR ENTERING PHYSICAL RECORDS INTO AN ELECTRONIC DATA STORE

(75) Inventor: Roy Schoenberg, Boston, MA (US)

(73) Assignee: CareKey, Inc., Boston, MA (US)

( * ) Notice: Subject to any disclaimer, the term of this patent is extended or adjusted under 35 U.S.C. 154(b) by 983 days.

(21) Appl. No.: 10/315,513

(22) Filed: Dec. 10, 2002

(65) Prior Publication Data

US 2004/0111297 A1    Jun. 10, 2004

(51) Int. Cl.
*G06K 7/10*    (2006.01)
(52) U.S. Cl. ............... 235/462.01; 707/102; 707/104.1; 707/10; 707/200
(58) Field of Classification Search ............... 235/ 462.01–462.49; 707/1, 10, 102, 104.1, 200; 705/2, 3
See application file for complete search history.

(56) References Cited

U.S. PATENT DOCUMENTS

| | | | |
|---|---|---|---|
| 6,192,165 B1 * | 2/2001 | Irons | 382/306 |
| 6,456,747 B2 * | 9/2002 | Altman | 382/305 |
| 6,674,924 B2 * | 1/2004 | Wright et al. | 382/306 |
| 6,854,641 B1 * | 2/2005 | Takagi | 235/375 |
| 6,959,308 B2 * | 10/2005 | Gramsamer et al. | 707/200 |
| 2003/0033319 A1 * | 2/2003 | Van Der et al. | 707/102 |
| 2004/0205466 A1 * | 10/2004 | Kuppinger et al. | 715/500 |
| 2006/0082822 A1 * | 4/2006 | Irons et al. | 358/1.15 |

\* cited by examiner

*Primary Examiner*—Michael G. Lee
*Assistant Examiner*—Daniel A. Hess
(74) *Attorney, Agent, or Firm*—Fulbright & Jaworski LLP

(57) ABSTRACT

A system for entering physical documents into an electronic data store includes a host server system having a computer processor and associated memory, including the electronic data store, a data entry system including a computer processor and associated memory and a provider system including a computer processor and associated memory. The data entry system transmits instructions to the host server system to generate a token including destination information for physical documents being entered into the electronic data store. The host server system includes a token generation system for generating the token, the token including the destination information for physical documents being entered into the electronic data store. The host server system transmits the token to the data entry system. The data entry system generates a hard copy of the token and transmits an electronic version of the hard copy of the token to the provider system. The provider system receives the electronic version of the token, converts the electronic version back to the hard copy of the token, attaches the physical documents to be entered in the electronic data store to the hard copy of the token and electronically transmits the hard copy and the physical documents to the host server system. The host server system receives the electronic form of the electronically transmitted hard copy and physical documents, reads the token and enters the electronic form of the physical documents into the electronic data store based on the destination instructions.

21 Claims, 2 Drawing Sheets

METHOD OF AND SYSTEM FOR ENTERING PHYSICAL RECORDS INTO AN ELECTRONIC DATA STORE

FIELD OF THE INVENTION

The invention relates generally to a method of and system for entering physical records into an electronic data store, and more particularly, to a method of and system for enabling an individual to update information records stored in an electronic format with records in a physical form.

BACKGROUND OF THE INVENTION

In the past, patient records, such as physician diagnoses and notes, test results, prescription forms, etc. were maintained in a physical file at the location where the patient was seen by the primary care physician. If the patient needed to see a specialist or visited an emergency room or walk-in clinic, the only way for the attending health care provider to obtain the patient's information would be to have the patient bring copies of the file or have the primary care physician's office forward the files to the attending health care provider by, for example, mail or facsimile, which of course is not necessarily an option in the emergency room. In such situations, the attending health care provider must rely on information provided by the patient or the patient's family or friends, which is subject to lapses of memory and misunderstandings of the patient's health history.

Recent advances in technology have spawned trends toward storing all types of documentation in an electronic format on databases that are accessible via local networks and the internet. However, when the issue of storing and transferring patient records in this manner is addressed several concerns have been raised by patients and the medical community. One concern is the mechanics involved in transferring physical paper records into an electronic data store. Manually entering the information is extremely tedious and time-consuming. Furthermore, many physicians are not necessarily willing to change the way that they keep their notes, which is still being done by "paper and pencil" for the most part, by entering their notes directly into the electronic data store.

SUMMARY OF THE INVENTION

The present invention is directed to a system that enables a patient or any other authorized person to enter records, documents, prescription orders, etc. that are in a paper form into an electronic record stored on a database associated with the data storage facility at which the patient's records are stored. The system generates an optically discernable token that is attached to the paper records which are to be entered into the electronic database and the paper record, including the token, is either sent to a server system via facsimile transmission or the paper record is scanned directly into the server system. The token includes information that identifies the person inputting the paper record and directs the server system to store an electronic form of the paper record in a particular electronic file.

According to one aspect of the invention, a method of entering physical documents into an electronic data store includes:

A. generating an optical token at a host server system, the optical token including destination information for physical documents being entered into the electronic data store;

B. transmitting the optical token to a recipient system;

C. generating a hard copy of the optical token;

D. electronically transmitting the hard copy and the physical documents to the host server system;

E. receiving a physical form of the electronically transmitted hard copy and physical documents; and F. the host server system reading the optical token and entering the physical documents into the electronic data store based on the destination instructions.

Step B may include transmitting the hard copy and the physical documents with a facsimile machine. The optical token may be a barcode or an encrypted number sequence. The method may further include, prior to step A, transmitting instructions to the host server system, the instructions including the destination information.

According to another aspect of the invention, a method of entering physical documents into an electronic data store includes:

A. generating an optical token at a host server system, the optical token including destination information for physical documents being entered into the electronic data store;

B. transmitting the optical token to a recipient system;

C. generating a hard copy of the optical token;

D. attaching the physical documents to be entered in the electronic data store to the hard copy of the optical token;

E. electronically transmitting the hard copy and the physical documents to the host server system;

F. receiving an electronic form of the electronically transmitted hard copy and physical documents; and G. the host server system reading the optical token and entering the electronic form of the physical documents into the electronic data store based on the destination instructions.

According to another aspect of the invention, a system for entering physical documents into an electronic data store includes a host server system including a computer processor and associated memory, including the electronic data store and a data entry system including a computer processor and associated memory. The host server system includes a token generation system for generating an optical token, the optical token including destination information for physical documents being entered into the electronic data store. The host server system transmits the optical token to the data entry system. The data entry system generates a hard copy of the optical token, associates the physical documents to be entered in the electronic data store to the hard copy of the optical token and electronically transmits the hard copy and the physical documents to the host server system. The host server system receives an electronic form of the electronically transmitted hard copy and physical documents, reads the optical token and enters the electronic form of the physical documents into the electronic data store based on the destination instructions.

The data entry system may further include a facsimile machine for transmitting the hard copy and the physical documents. The optical token may be a barcode or an encrypted number sequence. The data entry system, prior to the generation of the optical token, may transmit instructions to the host server system, the instructions including the destination information.

According to yet another aspect of the invention, a system for entering physical documents into an electronic data store includes a host server system having a computer processor and associated memory, including the electronic data store, a data entry system including a computer processor and associated memory and a provider system including a computer processor and associated memory. The data entry system transmits instructions to the host server system to generate a token including destination information for physical documents being entered into the electronic data store. The host server system includes a token generation system for generating the token, the token including the destination information for physical documents being entered into the electronic data store. The host server system transmits the token to the data entry system. The data entry system generates a hard copy of the token and transmits an electronic version of the hard copy of the token to the provider system. The provider system receives the electronic version of the token, converts the electronic version back to the hard copy of the token, attaches the physical documents to be entered in the electronic data store to the hard copy of the token and electronically transmits the hard copy and the physical documents to the host server system. The host server system receives the electronic form of the electronically transmitted hard copy and physical documents, reads the token and enters the electronic form of the physical documents into the electronic data store based on the destination instructions.

According to yet another aspect of the invention, a method of entering information into an electronic data store comprising:

A. generating an optical token at a host server system, the optical token including destination information for information which is to be entered into the electronic data store;

B. transmitting the optical token to a recipient system in the form of an electronic mail document;

C. entering, into a further electronic mail document including the optical token, the information to be entered into the electronic data store;

D. transmitting the further electronic mail document to the host server system;

E. receiving the further electronic mail document; and

F. reading the optical token and entering the information contained in the further electronic mail document into the electronic data store based on the destination instructions.

BRIEF DESCRIPTION OF THE DRAWINGS

The foregoing and other objects of this invention, the various features thereof, as well as the invention itself may be more fully understood from the following description when read together with the accompanying drawings in which.

DETAILED DESCRIPTION

The present invention enables a patient or other authorized person to enter a paper record including information about the patient into an electronic record including information about the patient. The system includes converting the paper document into an electronic format, and entering the information included on the document into the appropriate location in the electronic file based on an optical token which is affixed to a page of the paper document.

Figure 1:
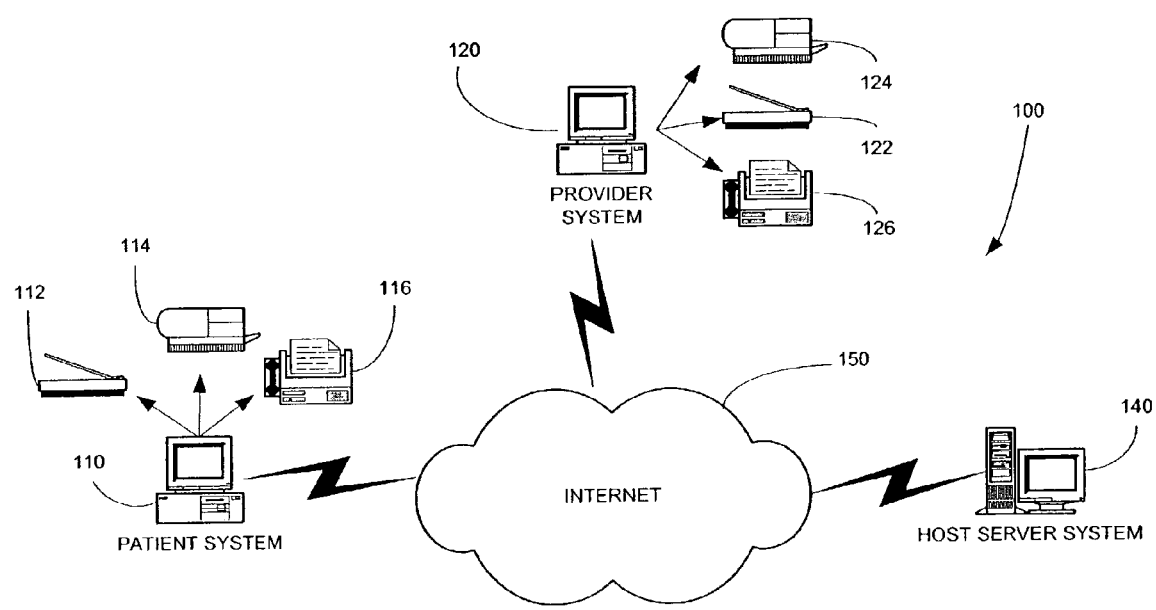
FIG. 1 is a diagrammatic view of a system for distributing medical information in accordance with the present invention.

FIG. 1 shows a diagram of a system 100 for entering a patient's paper-format records into an electronic data store accordance with a preferred embodiment of the present invention. The system 100 includes a patient system 110, provider system 120 and a host server system 140 all connected to a common communications network 150. Preferably, each of the patient system 110, provider system 120 and host server system 140 can each be a personal computer such as an IBM PC or IBM PC compatible system or an APPLE® MacINTOSH® system or a more advanced computer system such as an Alpha-based computer system available from Compaq Computer Corporation or SPARC® Station computer system available from SUN Microsystems Corporation, although a main frame computer system can also be used. Preferably, the communications channel 150 is a TCP/IP-based network such as the Internet or an intranet, although almost any well known LAN, WAN or VPN technology can be used.

In one embodiment of the invention, the patient system 110 and provider system 120 are IBM PC compatible systems operating a Microsoft Windows® operating system and host server system 140 is configured as a web server providing access to information such as web pages in HTML format via the HyperText Transport Protocol (http). The patient system 110 and provider system 120 include software to allow viewing of web pages, commonly referred to as a web browser, thus being capable of accessing web pages located on host server system 140. Furthermore, patient system 110, provider system 120 and host server system 140 include software for encrypting and decrypting data that is transmitted over the communications network 150. Patient system 110 and provider system 120 also each respectively include an optical scanner 112, 122 a printer 114, 124 and a facsimile machine 116, 126.

Alternatively, patient system 110 and provider system 120 can be any wired or wireless device that can be connected to a communications network, such as an interactive television system, such as WEBTV, a personal digital assistant (PDA) or a cellular telephone. In this preferred embodiment, patient system 110 is located at the patient's home and provider system 120 is located at primary care physician's office or wherever a patient's medical record is maintained or updated, such as in an emergency room or another doctor's office.

Figure 2:
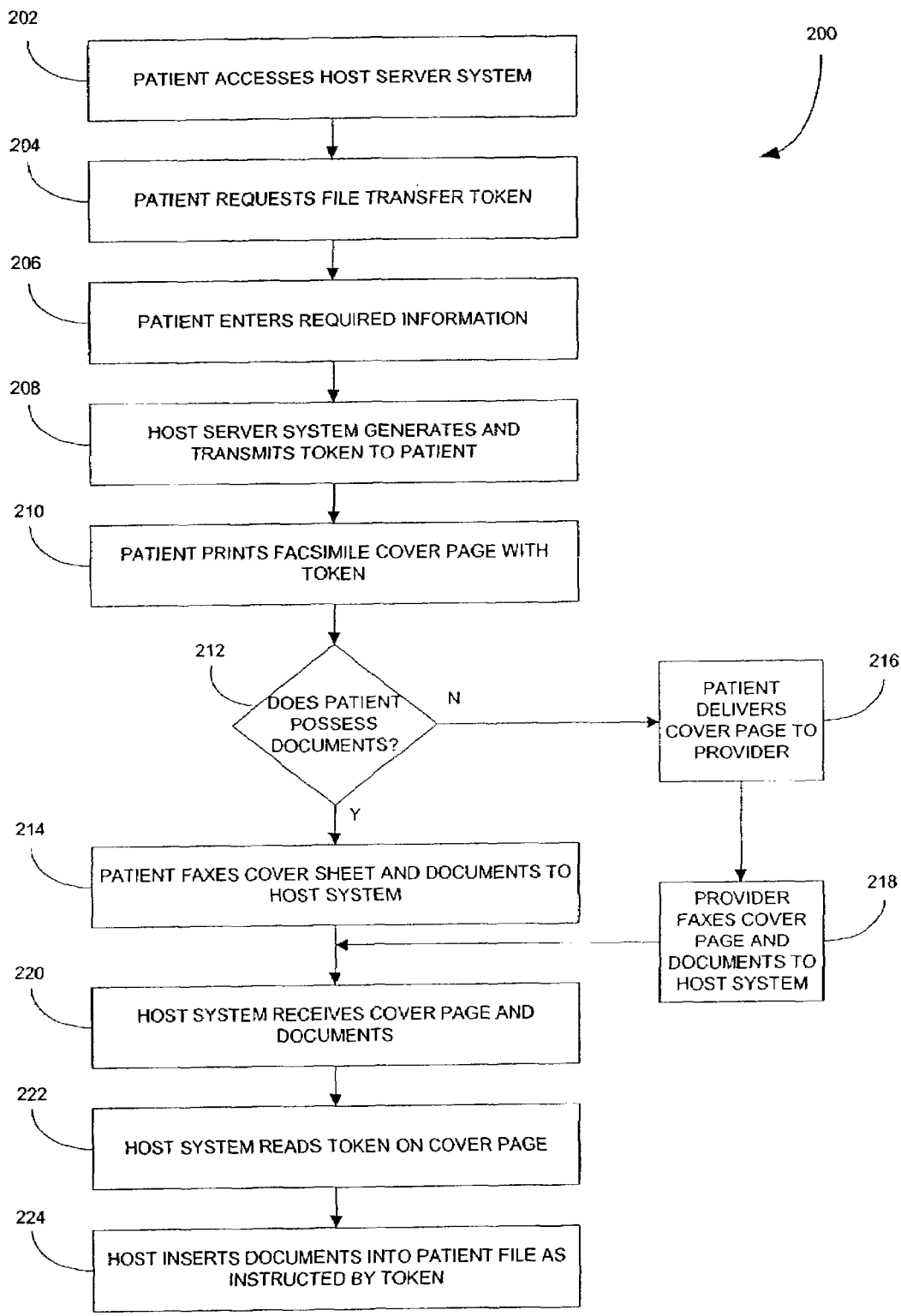
FIG. 2 is a flow diagram of a method of entering a paper record into an electronic data store in accordance with the present invention.

FIG. 2 is a flow diagram 200 showing the steps involved in a preferred embodiment of the present invention. Prior to the actions shown in FIG. 2, it will be understood that the patient has set up an account with the host server system, such that the patient is able to store his or her information records in the database associated with the host server system 140. The patient's account will typically include several folders for storing different types of medical information. In step 202, the patient, through patient system 110, accesses his or account on the host server system 140 via the internet 150. The patient then requests a file transfer token, step 204. The patient enters the required information, such as the destination file of the documents being transmitted to the host server system, rules desired by the patient and instructions to be carried out by the host server system. Rules input by the patient might include an expiration event of the token. For example, if the patient desires to use the same token for more than one document transmission or for a certain period of time, such rules may be input to the host server system by the patient. Instructions that may be input by the patient include instructing the host server system to send an acknowledgement when the transferred document has been successfully input to the patient's record, to notify the patient in the event that the record being transferred is accessed by another party, to deny access to the transmitted documents by certain parties, etc. Once the relevant information has been transmitted to the host server system 140, the host server system generates a token which is optically discernable when printed on a sheet of paper. This token includes all of the information necessary for the host server system to accept the electronic documents being transmitted thereto and to insert the documents into the proper place within the patient's record. Alternatively, the token can be a pointer to the location of the relevant information input by the patient that is stored on the host server system. Since the host server system actually generates the token, it is completely able to follow the instructions contained in the token when the token is returned thereto.

In one embodiment of the invention, the token is a bar code. However, it will be understood that any form of optically discernable token may be used, including 2-dimensional grid codes, encrypted number codes, etc. The code need only be capable of containing the relevant information, including the identity of the patient, an authorization for the host system to accept and process the transmitted documents, the destination of the transmitted documents, the processing rules associated with the transmission of the documents and the instructions for the host system regarding use of the received documents.

Once the host server system generates the token, it is transmitted to the patient system 110 via the internet, step 208. The patient then prints the token on a piece of paper, step 210, using printer 114, which paper will serve as a facsimile cover sheet in the following steps. If the patient has possession of the physical documents, step 212, he or she can fax the documents, using the token page as a fax cover sheet, to the host server system 40, using facsimile machine 116, step 214. If the patient does not have physical possession of the files, step 212, he or she will fax the token page to the provider system 120, or to whatever location has the physical files, step 216. The personnel at the provider system need only then attach the token page to the physical documents of the patient which are to be inserted into the patient's electronic record stored on the host server system database, and fax the documents to the host server system 140 using fax machine 126, step 218.

The faxed token page and documents are received by the host server system 140 in the electronic format, step 220, the host server system 140 converts the documents to a physical format, optically reads the token upon receipt of the token page from the patient or provider systems, step 222, and inserts the documents into the specific location of the patients file as instructed by the token, step 224.

In an alternative embodiment, the token page that is printed out by the patient in step 210 and the accompanying documents may be scanned into the patient system 110 or provider system 120 with scanners 112, 122, respectively, and the token page and documents can then be transmitted to the host server system 140 via the internet 150 in the form of an email, for example. Upon receipt, the host server system 140 will print out the documents and read the token to obtain the included instructions. Furthermore, tokens may be printed onto labels which are affixed directly to the documents, and the documents can then be faxed or otherwise transmitted to the host server system 140 without the need for a separate cover page. This embodiment may be preferred in the case where the patient does not have access to a computer or fax machine.

In a further embodiment of the invention, the host server system 140 is included within the provider system 120, such that the records stored in the electronic database of the host server system 140 are located proximate the provider system 120. The provider system 120 and/or the host server system can include an optical character recognition (OCR) system for enabling personnel to edit the patient's records after they have been received by the host server system 140 and entered into the electronic database.

According to another embodiment of the invention, specific documents may be preprinted for use for hand-writing or typing notes thereon. The preprinted documents include the optically-discernable token indicating where within a patient's electronic record the notes are to be inserted. For example, preprinted documents may be used for prescription orders. In this example, a physician could have a multiple-page writing pad of preprinted prescription orders, each page having an optical token that directs the order to be entered into a patient's prescription file when it is faxed or otherwise transmitted to the host server system 140. Such a document eliminates the need for printing out a separate token page or affixing a printed label on the records. However, because the preprinted documents are generic with regards to the specific patient receiving the document, the patient will have no input into rules or instructions contained in the token, as described above.

According to another embodiment of the invention includes embedding the token in the subject line of an email. When the email is received by the host server system, the token in the subject line is used by the host server system to determine where the information contained in the body of the email is to be stored. In such an embodiment, the patient requests the token from the host server system in the manner described above. The host server system then sends an email to the patient, with the token embedded in the subject line of the email. After receiving the email from the host server system, the patient need only enter the information that is to be stored in the electronic database of the host server system in the body of a reply email and send the reply email back to the host server system. When the reply email is received by the host server system, the token is retrieved from the subject line, read by the host server system and the information is entered into the appropriate location in the patient's record.

While the invention has been described in connection with paper-based medical records being entered into an electronic database, it will be understood that the system may be utilized for entering paper-based records including any type of information into an electronic database, such as academic records, employment records, etc.

The system and method may be embodied in other specific forms without departing from the spirit or essential characteristics thereof. The present embodiments are therefore to be considered in respects as illustrative and not restrictive, the scope of the system and method being indicated by the appended claims rather than by the foregoing description, and all changes which come within the meaning and range of the equivalency of the claims are therefore intended to be embraced therein.

The invention claimed is:

1. A method of entering physical documents into an electronic data store comprising:
   A. generating an optical token at a host server system, said optical token including destination information for physical documents being entered into the electronic data store;
   B. transmitting the optical token to a recipient system;
   C. generating a hard copy of said optical token;
   D. electronically transmitting said hard copy and said physical documents to said host server system;
   E. receiving a physical form of said electronically transmitted hard copy and the physical documents; and
   F. said host server system reading said optical token and entering said physical documents into said electronic data store based on said destination instructions.

2. The method of claim 1 wherein step B comprises transmitting said hard copy and said physical documents with a facsimile machine.

3. The method of claim 1 wherein said optical token is a barcode.

4. The method of claim 1 wherein said optical token is an encrypted number sequence.

5. The method of claim 1 further comprising, prior to step A, transmitting instructions to said host server system, said instructions including said destination information.

6. A method of entering physical documents into an electronic data store comprising:
   A. generating an optical token at a host server system, said optical token including destination information for physical documents being entered into the electronic data store;
   B. transmitting the optical token to a recipient system;
   C. generating a hard copy of said optical token;
   D. attaching the hard copy of said optical token to the physical documents to be entered in the electronic data store;
   E. electronically transmitting said hard copy and said physical documents to said host server system;
   F. receiving an electronic form of said electronically transmitted hard copy and physical documents; and
   G. said host server system reading said optical token and entering said electronic form of said physical documents into said electronic data store based on said destination instructions.

7. The method of claim 6 wherein step B comprises transmitting said hard copy and said physical documents with a facsimile machine.

8. The method of claim 6 wherein said optical token is a barcode.

9. The method of claim 6 wherein said optical token is an encrypted number sequence.

10. The method of claim 6 further comprising, prior to step A, transmitting instructions to said host server system, said instructions including said destination information.

11. A system for entering physical documents into an electronic data store comprising:
    a host server system including a computer processor and associated memory, including the electronic data store; and
    a data entry system including a computer processor and associated memory;
    said host server system including a token generation system for generating an optical token, said optical token including destination information for physical documents being entered into the electronic data store;
    said host server system transmitting said optical token to said data entry system;
    said data entry system generating a hard copy of said optical token, associating the physical documents to be entered in the electronic data store with said hard copy of said optical token and electronically transmitting said hard copy and said physical documents to said host server system; and
    said host server system receiving an electronic form of said electronically transmitted hard copy and physical documents and reading said optical token and entering said electronic form of said physical documents into said electronic data store based on said destination instructions.

12. The system of claim 11, said data entry system further comprising a facsimile machine for transmitting said hard copy and said physical documents.

13. The system of claim 11 wherein said optical token is a barcode.

14. The system of claim 11 wherein said optical token is an encrypted number sequence.

15. The system of claim 11 wherein said data entry system, prior to the generation of said optical token, transmits instructions to said host server system, said instructions including said destination information.

16. A system for entering physical documents into an electronic data store comprising:
    a host server system including a computer processor and associated memory, including the electronic data store;
    a data entry system including a computer processor and associated memory; and
    a provider system including a computer processor and associated memory;
    said data entry system transmitting instructions to said host server system to generate a token including destination information for physical documents being entered into said electronic data store;
    said host server system including a token generation system for generating said token, said token including said destination information for physical documents being entered into the electronic data store;
    said host server system transmitting said token to said data entry system;
    said data entry system generating a hard copy of said token and transmitting an electronic version of said hard copy of said token to said provider system;
    said provider system receiving said electronic version of said token, converting said electronic version back to said hard copy of said token, attaching the physical documents to be entered in the electronic data store to said hard copy of said token and electronically transmitting said hard copy and said physical documents to said host server system; and
    said host server system receiving the electronic form of said electronically transmitted hard copy and physical documents, reading said token and entering said electronic form of said physical documents into said electronic data store based on said destination instructions.

17. The system of claim 16, said data entry system further comprising a facsimile machine for transmitting said hard copy of said token and said physical documents.

18. The system of claim 16 wherein said token is a barcode.

19. The system of claim 16 wherein said token is an encrypted number sequence.

20. The system of claim 16, said provider system further comprising a facsimile machine for transmitting said hard copy of said token and said physical documents.

21. A method of entering information into an electronic data store comprising:
    A. generating an optical token at a host server system, said optical token including destination information for information which is to be entered into the electronic data store;
    B. transmitting the optical token to a recipient system in the form of an electronic mail document;
    C. entering, into a further electronic mail document including said optical token, said information to be entered into the electronic data store;
    D. transmitting said further electronic mail document to said host server system;
    E. receiving the further electronic mail document; and
    F. reading said optical token and entering said information contained in the further electronic mail document into said electronic data store based on said destination instructions.

* * * * *